United States Patent [19]
Akiyama

[11] Patent Number: 5,098,181
[45] Date of Patent: Mar. 24, 1992

[54] OPHTHALMIC MEASURING APPARATUS
[75] Inventor: Koichi Akiyama, Tokyo, Japan
[73] Assignee: Kowa Company Ltd., Japan
[21] Appl. No.: 458,095
[22] Filed: Dec. 28, 1989
[30] Foreign Application Priority Data
Dec. 28, 1988 [JP] Japan .................. 63-329377
Dec. 28, 1988 [JP] Japan .................. 63-329378
[51] Int. Cl.⁵ .............................................. A61B 3/10
[52] U.S. Cl. ................................... 351/221; 351/246; 351/214; 351/205
[58] Field of Search .................. 351/214, 221, 246; 128/745

[56] References Cited
U.S. PATENT DOCUMENTS
4,257,687 3/1981 Kohayakawa .................. 351/214
4,711,542 12/1987 Ichihashi et al. .................. 351/246

Primary Examiner—Paul M. Dzierzynski
Attorney, Agent, or Firm—Bruce L. Adams; Van C. Wilks

[57] ABSTRACT

An ophthalmic measuring apparatus in which a laser beam is projected at a selected spot in the eye and light scattered therefrom is received and processed for ophthalmic measurement. The light scattered from the selected spot in the eye is received by a photoelectric converter comprised of a plurality of avalanche photodiodes or by a photomultiplier via a liquid crystal video module comprised of a plurality of liquid crystal elements. Signals from the avalanche photodiodes or liquid crystal elements disposed at surrounding portions are subtracted from signals from those at the central portion to remove a noise component based on the light scattered from the portions surrounding the selected spot in the eye.

10 Claims, 5 Drawing Sheets

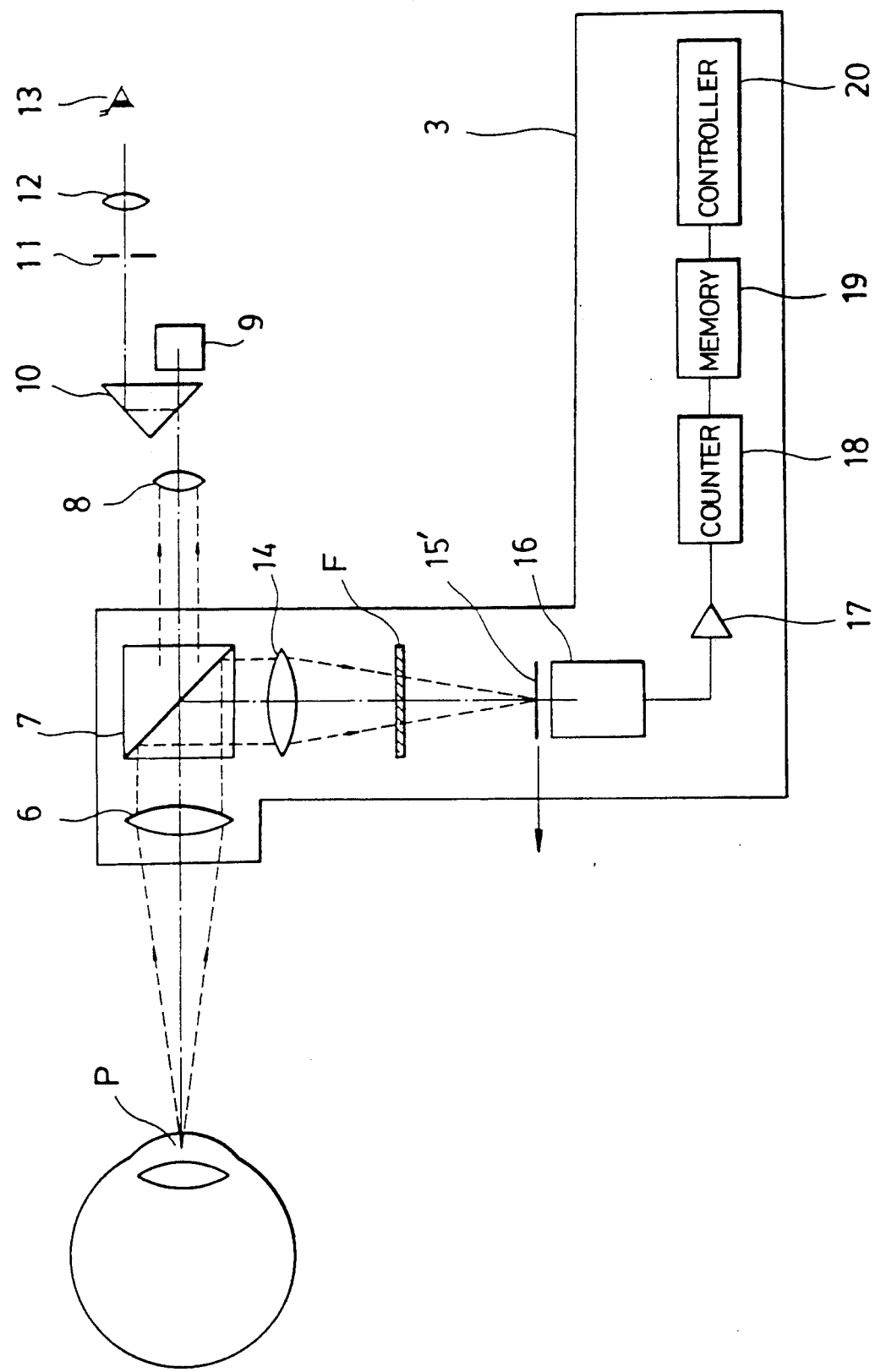

FIG. 7a
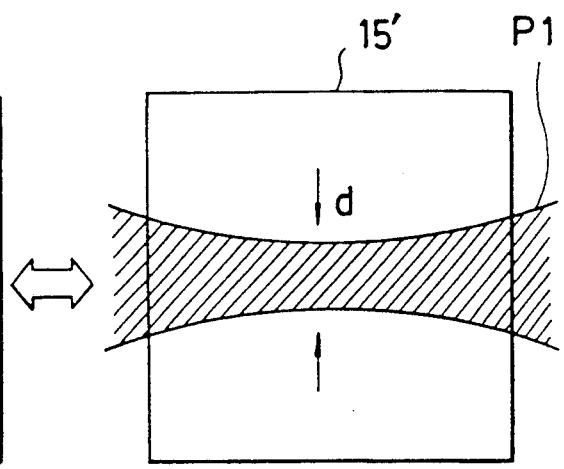
FIG. 7b
FIG. 8
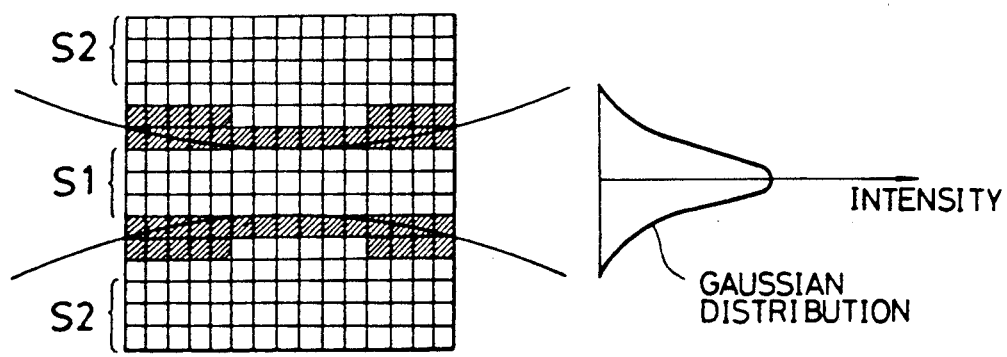

OPHTHALMIC MEASURING APPARATUS

BACKGROUND OF THE INVENTION

1. Field of the Invention

This invention relates to an ophthalmic measuring apparatus, and more particularly to an ophthalmic measuring apparatus for detecting ophthalmic diseases in which laser light is radiated via an optical system at one spot in the eye, particularly in the anterior chamber thereof, and the laser light scattered therefrom is analyzed to measure the ophthalmic diseases.

2. Description of the Prior Art

The measurement of protein concentration in the anterior chamber of the eye is of great importance in determining whether the eye is inflamed, that is, whether a blood-aqueous barrier functions normally or not. Conventionally, a slit lamp microscope is very often used to determine the turbidity by grading via the naked eye. On the other hand, a photographic measuring method has been developed to make a quantitative measurement.

The determination by naked eye depends upon an examiner and is not reliable in data. To overcome this problem, a method has been proposed in which a laser beam is radiated in the eye and the light scattered therefrom is received and analyzed quantitatively (see, for example, U.S. Pat. No. 4,711,542).

In such a measuring method, the scattered or diffused light from portions in the eye such as the cornea, iris, crystalline lens, artificial crystalline lens implanted after operation of cataract etc. enters as noise into the laser beam scattered from the eye or into the measured spot in the eye in receiving the laser beam scattered. This degrades measurement accuracy and reduces the reproducibility of measured values.

To reduce the noise due to the reflected or scattered light entering into the spot to be measured in the eye, the Japanese Laid-open Patent Publication No. 135128/88 or U.S. Pat. No. 4,832,043 discloses an apparatus in which a laser beam is deflected for scanning in the eye beyond the width of a slit on a mask disposed in front of the photoelectric converter. The output signal (including noise components) obtained when the laser beam is deflected beyond the slit width is subtracted from the output signal (including effective and noise components) when the laser beam passes across the slit width, thereby removing background noise from the cornea, crystalline and so on.

In another method, the mask is displaced to measure the quantity of light obtained when the laser beam is located at upper and lower portions of the mask. In the same manner, the subtraction from the laser-scattered light is performed to remove the background noise.

The utilization of such methods in the prior arts makes it possible to remove noise based on the dark current in the photoelectric converter or unnecessary scattered or reflected light contained in the signal from the photoelectric converter, thus providing an improved resolving power and improved accuracy of measurement.

In the first method, however, means for deflecting the laser beam are required, while needing means for displacing the mask in the second method. This disadvantageously makes the apparatus complicated and expensive. Furthermore, these methods necessitate moving parts, which eventually may degrade the reproducibility of measured data and guarantee no precise measurement of data with high accuracy.

SUMMARY OF THE INVENTION

It is, therefore, an object of the invention to provide an ophthalmic measurement apparatus being capable of reducing noise due to reflected or scattered light entering into the spot to be measured for improvement in accuracy of measurement.

According to one embodiment of the invention, there is provided an ophthalmic measuring apparatus in which a laser beam is projected at a selected spot in the eye and light scattered therefrom is received and processed for ophthalmic measurement, comprising a laser source for producing the laser beam, means for focusing the laser beam from the laser source at the selected spot in the eye, and photoelectric converting means for receiving light scattered from the selected spot in the eye and converting it into an electrical signal which is processed for ophthalmic measurement. In the apparatus the photoelectric converting means comprise a plurality of avalanche photodiodes arranged in an array at a portion which is a conjugate point relative to the selected spot in the eye.

In such an arrangement, the avalanche photodiode array is disposed at that portion in the light receiving means which is a conjugate point relative to the predetermined spot in the eye, and light scattered from the spot is introduced to the avalanche photodiode array via each of the avalanche photodiodes. This eliminates the necessity of deflecting the laser beam or displacing the mask, and enables the measurement of the noise due to the light scattered from the cornea, iris or crystalline lens.

Preferably, the avalanche photodiodes are arranged in such a manner that the avalanche photodiodes at a central portion receive the light scattered from the selected spot in the eye, while the other avalanche photodiodes receiving light scattered from portions surrounding the selected spot in the eye. Signals from the avalanche photodiodes other than the central portion are subtracted from signals from those at the central portion to remove a noise component based on the light scattered from the portions surrounding the selected spot in the eye. This reduces noise due to reflected or scattered light entering into the spot to be measured and improves in accuracy of measurement.

According to another embodiment of the invention, there is also provided an ophthalmic measuring apparatus in which a laser beam is projected at a selected spot in the eye and light scattered therefrom is received and processed for ophthalmic measurement, comprising a laser source for producing the laser beam, means for focusing the laser beam from the laser source at the selected spot in the eye, photoelectric converting means for receiving light scattered from the selected spot in the eye and converting it into an electrical signal which is processed for ophthalmic measurement, and a liquid crystal video module comprised of a plurality of liquid crystal elements arranged in a matrix at that portion in front of the photoelectric converting means which is a conjugate point relative to the selected spot in the eye, each of said liquid crystal elements being activated to transmit the light impinging thereon into the photoelectric converting means.

In this embodiment, the liquid crystal video module is disposed in front of the photoelectric converting means at a portion which is a conjugate point relative to the predetermined spot in the eye, and light scattered from the spot is introduced through each of the liquid crystal elements onto the photoelectric converter. This also eliminates the necessity of deflecting the laser beam or displacing the mask, and yet enables the measurement of the noise as in the previous embodiment.

BRIEF DESCRIPTION OF THE DRAWINGS

The objects and features of the present invention will become more apparent from the accompanying drawings and the following detailed description of the invention.

FIG. 5 is a vertical cross section of the apparatus according to another embodiment of the invention;

FIG. 7a is an illustrative view showing the light intensity distribution in the memory;

FIG. 7b is an illustrative view showing an image of the laser beam with the liquid crystal video module; and FIG. 8 is an illustrative view showing the light intensity distribution in a liquid crystal video module having finer picture elements.

DETAILED DESCRIPTION OF THE PREFERRED EMBODIMENTS

The invention will now be described in detail with reference to the drawings.

Figure 1:
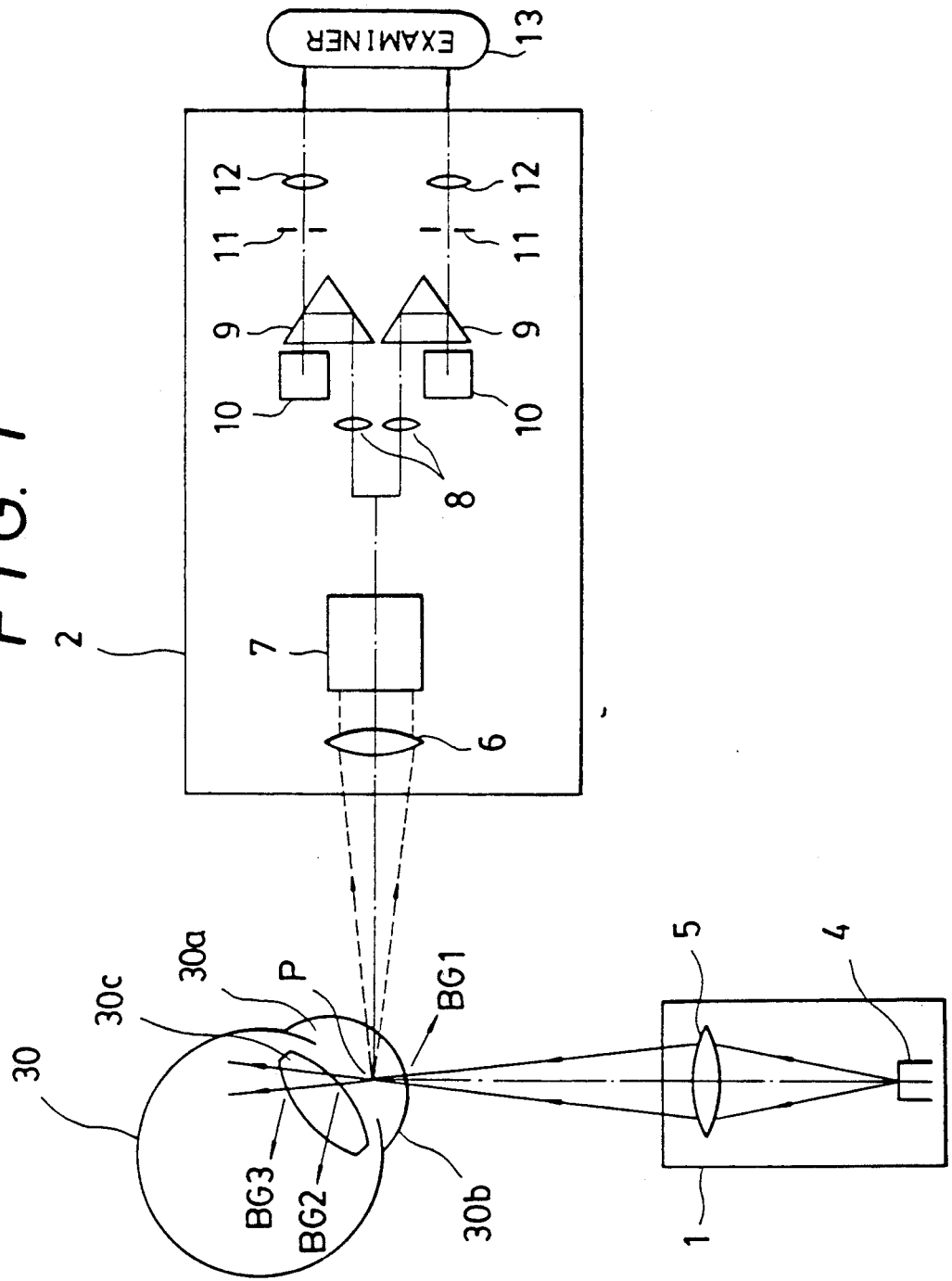
FIG. 1 is a horizontal cross section showing the arrangement of an ophthalmic measuring apparatus according to one embodiment of the invention.
Figure 2:
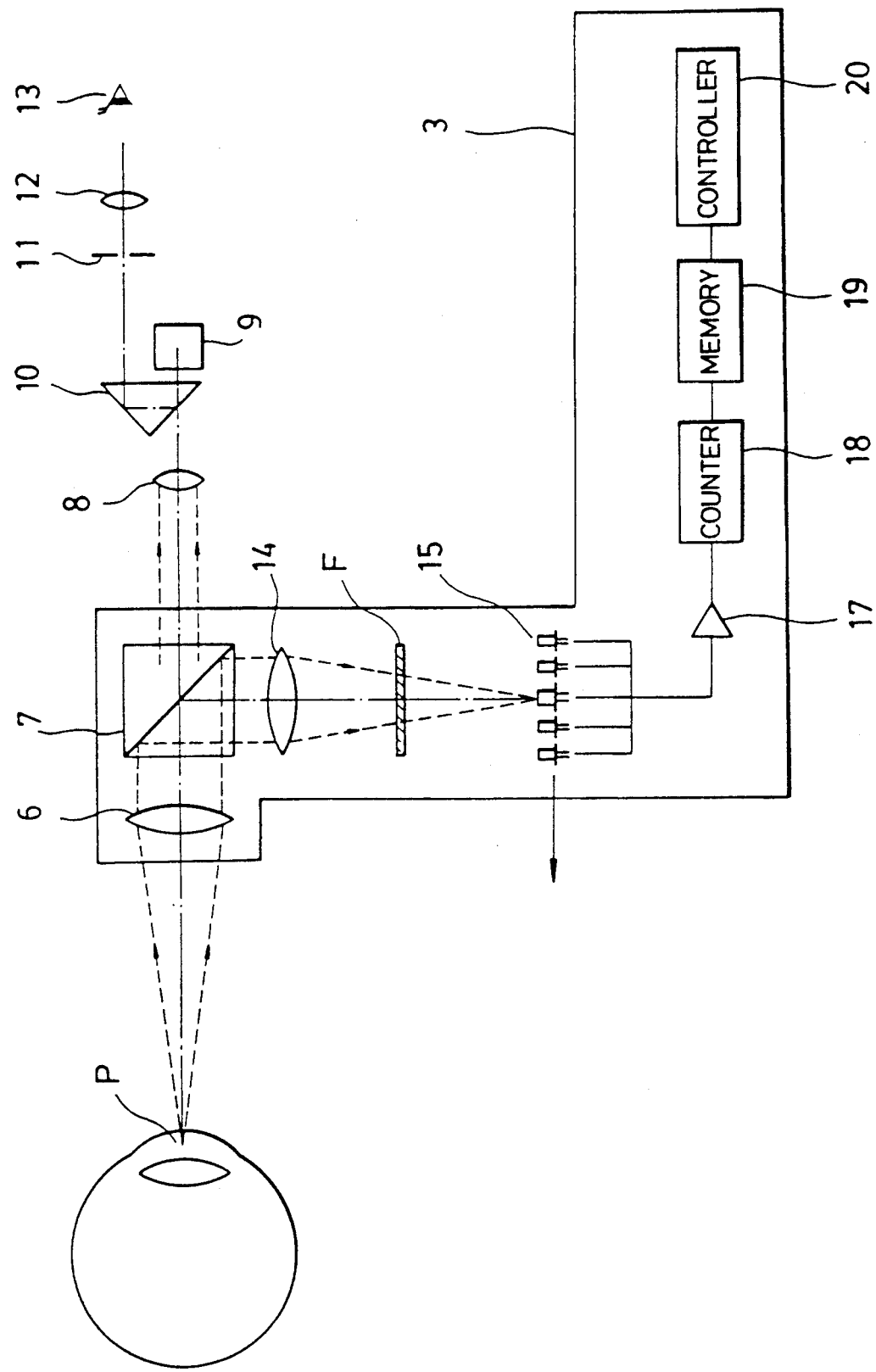
FIG. 2 is a vertical cross section of the apparatus in FIG. 1.

In FIGS. 1 and 2, which show an arrangement of the ophthalmic measuring apparatus according to the present invention, reference numeral 1 denotes a laser beam projector, in which a laser light source 4 such as, for example, a helium-neon or argon laser source is accommodated together with a condenser lens 5. Light from the laser light source 4 is passed through the condenser lens 5 to converge on the eye 30 under examination at a spot P in the anterior chamber 30a thereof.

The laser beam projector 1 is provided with a slit light source (not shown). Light from the slit light source passes via a slit to form a slit image on the anterior chamber 30a of the eye. This slit image is for illuminating the surrounding area to facilitate confirmation of the position of the spot of converged laser light.

Figure 3:
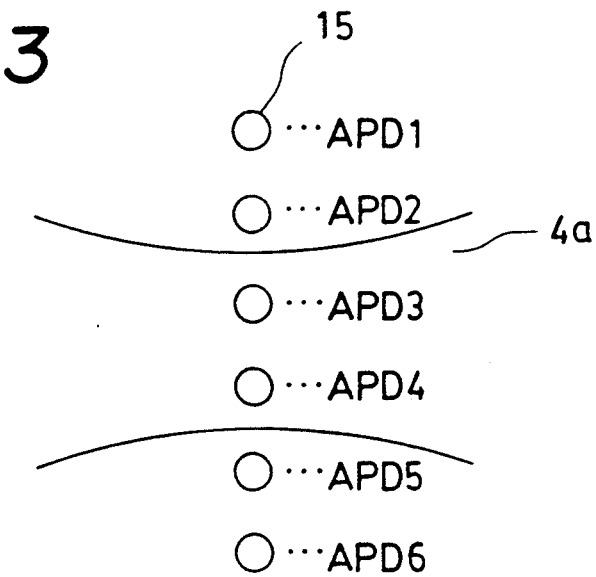
FIG. 3 is an illustrative view showing the arrangement of an avalanche photodiode array.

A portion of the laser light scattered from the measuring spot P in the anterior chamber 30a of the eye passes in a light receiving section 3 through a lens 6, a beam splitter 7, a lens 14, and an interference filter F and impinges on an avalanche photodiode array 15. The interference filter F is a kind of narrow-band filter which only passes the wavelength of the laser beam therethrough. The avalanche photodiode array 15 is, as shown in FIG. 3, comprised of a plurality of avalanche photodiodes APD1 to APD6 arranged in an array. The avalanche photodiode array 15 is disposed at that point in the light receiving section 3 which is a conjugate point relative to the convergence point P. The avalanche photodiodes APD1 to APD6 produce an output signal in response to the intensity of light impinging thereon and are disposed on the conjugate point of the convergence point P so that about one third of the avalanche photodiodes can be irradiated with the impinging laser beam 4a.

The output from the avalanche photodiode array 15 is fed through an amplifier 17 to a counter 18 connected to a controller 20 and the intensity of the scattered light detected by the avalanche photodiode array 15 is counted as numbers of pulses per unit time period. The output of the counter 18, i.e., the number of samplings or the total pulse count, is stored in memory cells in a memory 19 allocated for each unit time period. This process is carried out for every avalanche photodiode to produce a map representing the intensity distribution. The measured data stored in the memory 19 are processed in the controller 20 to evaluate the concentration of protein in the anterior chamber of the eye.

An observation section 2 serves to observe how the laser beam is projected in the eye, and includes a lens 6, a beam splitter 7 (the lens 6 and beam splitter 7 also shared by the light receiving section 3), a lens 8, prisms 9 and 10, a field stop 11 and an eyepiece 12 by which an examiner 13 carries out observations.

The operation of the apparatus arranged thusly will now be described. In conducting the measurement, the laser light source 4 is activated to emit a laser beam, which is converged on the measuring point P of the anterior chamber 30a in the eye. The light scattered from the measuring point P passes through the lens 6, and a portion of the scattered light is directed by the beam splitter 7 to the examiner 13 for observation through the lens 8, prisms 9 and 10, field stop 11 and lens 12.

The light scattered from the measuring point P and divided by the beam splitter 7 simultaneously passes through the lens 14 and the interference filter F and impinges on the avalanche photodiode array 15.

Each of the avalanche photodiodes APD1 to APD6 produces an output depending upon the quantity of light impinging thereon (the intensity of light scattered from the eye). The intensity of the scattered light detected by the avalanche photodiodes APD1 to APD6 is counted as numbers of pulses per unit time period. The output of the counter 18, i.e., the number of samplings or the total pulse count, is stored in the memory cells in the memory 19 allocated for each unit time period. This process is carried out for every avalanche photodiode to produce a map representing the intensity distribution in terms of all of the avalanche photodiodes.

When the laser beam is projected at the measuring point P as shown in FIG. 1, scattered light BG1 is generated when the laser beam hits the cornea 30b, and scattered light BG2 and BG3 when the laser beam passes through the front and rear surfaces of the crystalline lens 30c. These rays appear as noise and impinge on the avalanche photodiode array 15 together with the effective component from the measuring point P. In FIG. 3, the avalanche photodiodes APD1, APD2, APD5 and APD6 receive the scattered light based on the noise components, while the avalanche photodiodes APD3 and APD4 at the central area receives the scattered light based on the total of the effective and noise components.

The signals from the avalanche photodiodes APD3 and APD4 contains signal components corresponding to the protein concentration in the anterior chamber of the eye and the noise components based on the reflection and scattering other than the measuring point in the anterior chamber of the eye. Assuming that the average value of these outputs in the memory 19 be X, the controller 20 subtracts from the average value X the average value Y of the noise components based on the signals from the avalanche photodiodes APD1, APD2, APD5, and APD6 to extract the effective signal component and calculate the protein concentration in the anterior chamber of the eye.

Figure 4:
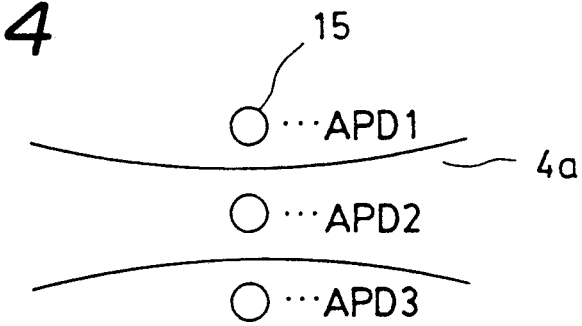
FIG. 4 is an illustrative view showing the arrangement of another avalanche photodiode array.

For a simpler embodiment, three avalanche photodiodes APD1 to APD3 are used as shown in FIG. 4. In this embodiment, the subtracting circuit can directly output a value APD2−(APD1+APD3)/2, so that the memory can be omitted. This reduces the cost of the apparatus, and further enables the reduction of the measurement time. The reduction in the measurement time also decreases the harmful influence coming from the blinking or slight movement of the patient's eye and reduces a burden to the patient, thus contributing to the measurement of precise data.

In misalignment between the ophthalmic measuring apparatus and the eye under examination, the output signals from the avalanche photodiodes APD1 and APD3 are often not equal to each other. Therefore, the avalanche photodiodes APD1 to APD3 are always monitored to find a state in which the signals from the avalanche photodiodes APD1 and APD3 are virtually the same to attain the alignment between the apparatus and the patient's eye. The measurement in such a state assuredly reduces a measurement error based on the miss-alignment.

In the above embodiment, the avalanche photodiode array is one-dimensional, but may be two-dimensional in the form of a matrix to improve the measurement accuracy.

FIG. 5 shows another embodiment of the invention, in which a conventional type of photomultiplier 16 is used as light receiving means and a liquid crystal video module 15' is disposed in front of the photomultiplier 16 at a portion which is a conjugate point of the convergence point P.

Figure 6:
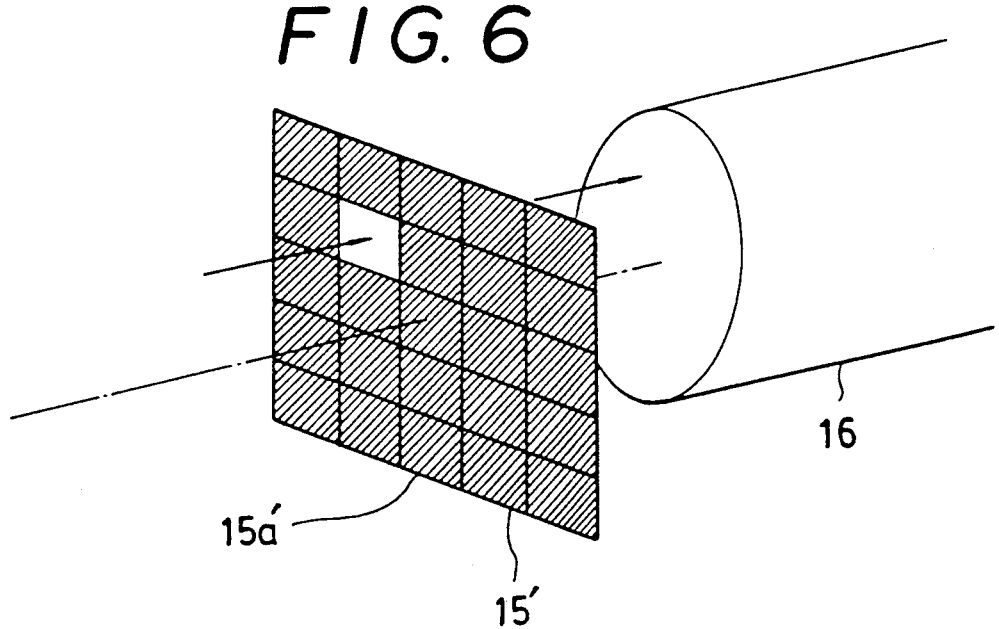
FIG. 6 is an illustrative view showing the arrangement of a liquid crystal video module.

The liquid crystal video module 15' is, as shown in FIG. 6, comprised of a plurality of liquid crystal elements 15a' which are all made of liquid crystal and arranged in a matrix. The liquid crystal video module 15' is disposed at that point in the light receiving section 3 which is a conjugate point relative to the convergence point P. Each of the liquid crystal elements in the liquid crystal video module functions as a shutter and permits the laser beam impinging to pass therethrough onto the photomultiplier 16.

The output from the photomultiplier 16 is passed through amplifier 17 and is fed to counter 18 connected to controller 20 and the intensity of the scattered light detected by the photomultiplier 16 is counted as numbers of pulses per unit time period. The output of the counter 18, i.e., the number of samplings or the total pulse count, is stored in memory cells in memory 19 allocated for each unit time period. As will be described later, this process is carried out for every liquid crystal element 15a' in the liquid crystal video module and repeated for all the liquid crystal elements to measure the intensity distribution on the liquid crystal video module, which is stored in the form of map data in the memory 19. The measured data stored in the memory 19 are processed in the controller 20 to evaluate the concentration of protein in the anterior chamber.

In operation, each of the liquid crystal elements in the liquid crystal video module 15' functions as a kind of shutter and is sequentially one from another activated on and off to permit the light scattered in the eye to pass therethrough. The quantity of light (scattered light intensity) passing through each liquid crystal element is received by the photomultiplier 16 and stored in the memory 19 in the form of time-course data to produce a map of data representing the intensity distribution.

As described earlier, when the laser beam is projected at the measuring point P, the scattered light BG1 is generated when the laser beam hits the cornea 30b, and the scattered light BG2 and BG3 when the laser beam passes through the front and rear surfaces of the crystalline lens 30c. These rays function as noise and impinge on the photomultiplier 16 together with the effective component from the measuring point P. Thus, the memory 19 includes a distribution region S2 based on the background (noise) components and a distribution region S1 based on the total of the effective and noise components, as shown in FIG. 7a.

It will be noted that the liquid crystal video module is selected so that it is much greater in size than an image P1 of the laser beam having a diameter d.

The distribution region S1 in FIG. 7a contains the signal component corresponding to the protein concentration in the anterior chamber of the eye and the noise components based on the reflection and scattering at the surrounding area. Assuming that the average intensity of the values in this region of the memory 19 be X, the controller 20 subtracts the average intensity Y of the noise in the region S2 from the average intensity X to extract the effective signal component and calculate the protein concentration in the anterior chamber.

Actually, the liquid crystal elements of the liquid crystal video module are so fine as shown in FIG. 8 that the intensity distribution of the laser beam shows a Gaussian distribution with a region having an intermediate value between the values in the regions S1 and S2, as shown by shaded portions. These shaded portions are taken neither as the region S1 nor as the region S2, so that the intensity values in these regions are omitted from the calculation.

In the embodiments above described, it is to be noted that it is preferable to perform the measurement again because of a high possibility of misalignment if there is a difference between the values in the upper portion S2 and the lower portion S2 of the laser beam image in FIGS. 7a and 8.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmic measuring apparatus in which a laser beam is projected at a selected spot in the eye and light scattered therefrom is received and processed for ophthalmic measurement, comprising:
   a laser source for producing the laser beam;
   means for focusing the laser beam from the laser source at the selected spot in the eye;

photoelectric converting means for receiving light scattered from the selected spot in the eye and converting it into an electrical signal which is processed for ophthalmic measurement;

wherein said photoelectric converting means comprises a plurality of avalanche photodiodes arranged in an array at a portion which is a conjugate point relative to the selected spot in the eye and wherein said avalanche photodiodes are arranged in such a manner that the avalanche photodiodes at a central portion receive the light scattered from the selected spot in the eye, while the other avalanche photodiodes receive light scattered from portions surrounding the selected spot in the eye; and means for subtracting signals from the avalanche photodiodes other than those at the central portion from signals from those at the central portion to remove a noise component based on the light scattered from the portions surrounding the selected spot in the eye.

2. An ophthalmic measuring apparatus in which a laser beam is projected at a selected spot in the eye and light scattered therefrom is received and processed for ophthalmic measurement, comprising:

a laser source for producing the laser beam;

means for focusing the laser beam from the laser source at the selected spot in the eye;

photoelectric converting means for receiving light scattered from the selected spot in the eye and converting it into an electrical signal which is processed for ophthalmic measurement; and a liquid crystal video module comprised of a plurality of liquid crystal elements arranged in a matrix at that portion in front of the photoelectric converting means which is a conjugate point relative to the selected spot in the eye, each of said liquid crystal elements being activated to transmit the light impinging thereon into the photoelectric converting means.

3. An apparatus as set forth in claim 2, wherein said liquid crystal video module is arranged in such a manner that the liquid crystal elements at a central portion receive the light scattered from the selected spot in the eye, while the other liquid crystal elements receiving light scattered from portions surrounding the selected spot in the eye.

4. An apparatus as set forth in claim 3, further comprising means for subtracting signals from the liquid crystal elements other than the central portion from signals from those at the central portion to remove a noise component based on the light scattered from the portions surrounding the selected spot in the eye.

5. An ophthalmic measuring apparatus, comprising:

means for producing a light beam and for focusing the beam at a selected spot in an eye; and means receptive of light scattered from the selected spot in the eye for converting the light into an electrical signal corresponding thereto, said means comprising an array of avalanche photodiodes having an intermediate portion and disposed at a conjugate point relative to the selected spot in the eye and positioned with the intermediate portion in a path of light scattered from the selected spot in the eye such that other portions of the array receive light scattered from portions surrounding the selected spot in the eye, and means for subtracting signals produced by photodiodes in the other portions of the array from the signals produced by photodiodes in the intermediate portion of the array to produce said electrical signal.

6. The apparatus according to claim 5, wherein the means for subtracting comprises a counter and a memory for storing a count from the counter.

7. An ophthalmic measuring apparatus, comprising:

means for producing a light beam and focusing the light beam at a selected spot in the eye;

light converting means receptive of light scattered from the selected spot in the eye for converting the light into an electrical signal;

a matrix of liquid crystal elements disposed upstream of the light converting means at a conjugate point relative to the selected spot in the eye; and means for activating each element of the matrix to transmit light impinging thereon onto the light converting means.

8. The apparatus according to claim 7, wherein the matrix has an intermediate portion in a path of light scattered from the selected spot in the eye and other portions in a path of light scattered from portions surrounding the selected spot in the eye.

9. The apparatus according to claim 8, further comprising means for subtracting signals produced by the light converting means from light transmitted through the other portions of the matrix from signals produced by the light converting means from light transmitted through the intermediate portion of the matrix.

10. The apparatus according to claim 9, wherein the means for subtracting comprises a counter and a memory for storing a count from the counter.

* * * * *